United States Patent [19]
Barry et al.

[11] Patent Number: 5,536,653
[45] Date of Patent: Jul. 16, 1996

[54] TOMATO FRUIT PROMOTERS

[75] Inventors: Gerard F. Barry; Janice W. Edwards, both of St. Louis; Ganesh M. Kishore, Chesterfield; David M. Stark, Fenton, all of Mo.

[73] Assignee: Monsanto Company, St. Louis, Mo.

[21] Appl. No.: 334,639

[22] Filed: Nov. 4, 1994

[51] Int. Cl.⁶ .......................... C12N 15/29; C12N 15/82; C12N 5/04; C12N 5/10

[52] U.S. Cl. ................. 435/172.3; 435/69.1; 435/70.1; 435/194; 435/240.4; 536/24.1; 536/24.5; 800/205; 800/DIG. 44

[58] Field of Search .................................. 435/69.1, 70.1, 435/172.3, 240.4, 194; 536/24.1, 24.5; 800/205, DIG. 44

[56] References Cited

U.S. PATENT DOCUMENTS 4,943,674  7/1990  Houck ..................................... 800/205

FOREIGN PATENT DOCUMENTS 9119806  12/1991  WIPO ............................. C12N 15/82

OTHER PUBLICATIONS

Bevan et al., The Structure and Transcription Start Site of a Major Potato Tuber Protein Gene. Nucleic Acids Research 14(11)4625–4638 (1986).
Muller-Rober et al., One of Two Different ADP-glucose Pyrophosphorylase Genes from Potato Responds Strongly to Elevated Levels of Sucrose. Mol. Gen. Genet. 224:136–146 (1990).
Picton et al., cDNA Cloning and Characterisation of Novel Ripening–Related mRNAs with Altered Patterns of Accumulation in the Ripening Inhibitor (RIN) Tomato Ripening Mutant. Plant Mol. Bio. 23:193–207 (1993).
Nakata et al., 1992. J. Cell. Biochem. Suppl. 16F:226.
Ganal et al. 1991. Mol. General Genetics 225(3):501–509.
Koster-Topfer et al. 1989. Mol. Gen. Genet. 219:390–396.

*Primary Examiner*—David T. Fox
*Attorney, Agent, or Firm*—Grace L. Bonner; Dennis R. Hoerner, Jr.

[57] ABSTRACT

Promoters isolated from potato which cause expression of a gene of choice in tomato; tomato plant cells and plants containing them.

14 Claims, No Drawings

TOMATO FRUIT PROMOTERS

BACKGROUND OF THE INVENTION

Recent advances in genetic engineering have provided the requisite tools to transform plants to contain foreign genes. It is now possible to produce plants which have unique characteristics of agronomic and crop processing importance. The ability to chose the tissues in which to express such foreign genes and the time during plant growth to obtain expression is possible through the choice of a regulatory sequence which turns on the gene, called the promoter. A wide range of promoters are known for various plants, plant tissues, and developmental stages.

The tomato is a very important plant for genetic engineering. It is readily transformed to express foreign genes and has many characteristics which are known to be improved by certain genes. It is also a valuable crop plant in many countries and was the first transgenic food crop approved for sale in the U.S.

Promoters useful in expressing foreign genes in tomato and other fruits are known. For example, U.S. Pat. No. 4,943,674 (Houck et al., Jul. 24, 1990, incorporated herein by reference) discloses the 2A11 promoter as useful in expression of a heterologous gene in tomato fruit. The E4 and E8 promoters (Deikman, et al. (1988) *The EMBO Journal* 7:3315–3320), as well as the promoter for polygalacturonase are known to be fruit specific. However, there is a need for additional strong promoters which will cause expression of a gene in tomato fruit, particularly those having varying expression patterns through the growth and maturity of the fruit.

It is an object of the present invention to provide promoters which will function as fruit-specific in tomatoes. It is a still further object of the present invention to provide tomato plant cells and plants containing these promoters and genes encoding desired proteins or antisense sequences for down-regulating proteins or sense expression for co-suppression of protein production.

SUMMARY OF THE INVENTION

The present invention provides a method of obtaining expression of proteins in a fruit-enhanced manner in tomatoes by the use of promoters isolated from potatoes. These promoters have surprisingly been found to function in tomato cells to provide a high level of expression of a desired protein or antisense mRNA.

The present invention also provides transformed tomato plant cells containing a recombinant, double-stranded DNA molecule comprising in sequence:
 (a) a promoter selected from the group consisting of potato patatin promoters, potato ADPGPP promoters, and potato granule bound starch synthase promoters;
 (b) a structural DNA sequence that causes the production of an RNA sequence; and
 (c) a 3' non-translated region which functions in plant cells to cause transcriptional termination and the addition of polyadenylated nucleotides to the 3' end of the RNA sequence,
wherein said promoter is heterologous with respect to said structural DNA. Whole tomato plants containing this DNA construct are also provided.

As used herein, the term "fruit-enhanced" means functioning most strongly or exclusively in fruit tissue or cells.

As used herein, the term "potato patatin promoter(s)" means a promoter, isolated from a potato genome, associated with the DNA which encodes a patatin protein.

As used herein, the term "potato ADPGPP promoter(s)" means a promoter, isolated from a potato genome, associated with the DNA which encodes either the large or small subunit of the enzyme complex ADPglucose pyrophosphorylase.

As used herein, the term "potato granule bound starch synthase promoter(s)" means a promoter, isolated from a potato genome, associated with the DNA which encodes a granule bound starch synthase.

DETAILED DESCRIPTION OF THE INVENTION

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA.

Transcription of DNA into mRNA is regulated by a region of DNA usually referred to as the promoter. The promoter region contains a sequence of bases that signals RNA polymerase to associate with the DNA, and to initiate the transcription of mRNA using one of the DNA strands as a template to make a corresponding complimentary strand of RNA.

Surprisingly it has been found that certain promoters from potato will cause transcription of DNA in the fruit of tomatoes. Particularly of interest are promoters which normally cause preferential expression in the tubers. These include patatin promoters, ADPGPP promoters, and granule bound starch synthase promoters.

The expression pattern of these promoters in tomato fruit can be confirmed by fusion to the β-glucuronidase (GUS) gene and by following the expression of the GUS enzyme during development in transgenic fruit. Results are given below in Example 1.

These promoters have also been fused to the CTP-glgC16 construct described in WO 91/19806 (Kishore et al., corresponding to U.S. Ser. No. 08/120,703, incorporated herein by reference), which increases ADPglucose pyrophosphorylase activity. Results of transformation of tomatoes with three of these constructs are shown in Example 2. Alternatively, in order to increase sucrose content in fruit, one might want to inhibit the action of the native plant ADPGPP gene(s) by incorporating an antisense sequence (or a sense sequence for cosuppression) corresponding to one or both of the subunits of the native ADPGPP behind a promoter of the present invention.

Other genes which might be usefully fused to a promoter of the present invention include sucrose phosphate synthase (SPS), which is thought to control the overall rate of sucrose biosynthesis in plant cells, and sucrose synthase. Expression of an SPS or sucrose synthase gene, driven by a promoter of the present invention, may result in a developing fruit with stronger sink activity.

Another possible use is with an invertase gene. Expression of invertase in a sink cell such as in a fruit is another method for increasing the ability of a cell to act as a stronger sink by breaking down sucrose to metabolites that can be used in carbon utilization pathways, e.g., starch biosynthesis. More sucrose is then mobilized into the sink tissue.

Alternatively, the promoters may be used to drive genes which alter the ripening characteristics of fruit, such as ACC synthase or ACC deaminase. There may be many other genes which need fruit-specific promoters of varying strengths and growth profiles, for which the promoters of the present invention would be very useful.

Other promoters which drive expression of proteins found in tubers would also be expected to work in tomato plants with preferential expression in fruit. A number of such genes with tuber-specific or -enhanced expression, from which the promoters can be obtained, are known. These include the sucrose synthase gene (Salanoubat and Belliard, 1987, 1989) and the major tuber proteins including the 22 kd protein complexes and proteinase inhibitors (Hannapel, 1990). Other promoters which are contemplated to be useful in tomato fruit expression include those that show enhanced or specific expression in potato tubers, that are promoters normally associated with the expression of starch biosynthetic or modification enzyme genes, or that show different patterns of expression within the potato tuber. Examples of these promoters include those for the genes for soluble starch synthase, the branching enzymes, diproportionating enzyme, debranching enzymes, amylases, starch phosphorylases, pectin esterases, the 40 kD glycoprotein, ubiquitin, aspartic proteinase inhibitor, the carboxypeptidase inhibitor, tuber polyphenol oxidases, putative trypsin inhibitor and other tuber cDNAs.

Plant Transformation/Regeneration

A double-stranded DNA molecule containing one of the promoters of the present invention can be inserted into the genome of a plant by any suitable method. Suitable plant transformation vectors include those derived from a Ti plasmid of *Agrobacterium tumefaciens*, as well as those disclosed, e.g., by Herrera-Estrella, et al. (1983) Nature 303:209; Klee, H. J., et al. (1985) *Bio/Technology* 3:637–42; and EPO publication 120,516 (Schilperoort et al.). In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen.

A particularly useful Agrobacterium-based plant transformation vector for use in transformation of dicotyledonous plants is plasmid vector pMON505 (Rogers, S. G. et al. (1987) "Improved Vectors for Plant Transformation: Expression Cassette Vectors and New Selectable Markers" in *Methods in Enzymology*, ed. Wu and Grossman, pp 253–277, San Diego: Academic Press). Binary vector pMON505 is a derivative of pMON200 in which the Ti plasmid homology region, LIH, has been replaced with a 3.8 kb HindIII to SmaI segment of the mini RK2 plasmid, pTJS75 (Schmidhauser, T. J. and D. R. Helinski. (1985) *J. Bacteriol.* 164–155). This segment contains the RK2 origin of replication, oriV, and the origin of transfer, oriT, for conjugation into Agrobacterium using the tri-parental mating procedure (Horsch, R. B. and H. Klee. (1986) *PNAS U.S.A.* 83:4428–32). Plasmid pMON505 retains all the important features of pMON200 including the synthetic multi-linker for insertion of desired DNA fragments, the chimeric NOS/NPTII/NOS gene for kanamycin resistance in plant cells, the spectinomycin/streptomycin resistance determinant for selection in *E. coli* and *A. tumefaciens*, an intact nopaline synthase gene for facile scoring of transformants and inheritance in progeny and a pBR322 origin of replication for ease in making large amounts of the vector in *E. coli*. Plasmid pMON505 contains a single T-DNA border derived from the right end of the pTiT37 nopaline-type T-DNA. Southern analyses have shown that plasmid pMON505 and any DNA that it carries are integrated into the plant genome, that is, the entire plasmid is the T-DNA that is inserted into the plant genome. One end of the integrated DNA is located between the right border sequence and the nopaline synthase gene and the other end is between the border sequence and the pBR322 sequences.

Another particularly useful Ti plasmid cassette vector is pMON-17227. This vector is described by Barry et al. in WO 92/04449 (corresponding to U.S. Ser. No. 07/749,611, now abandoned incorporated herein by reference) and contains a gene encoding an enzyme conferring glyphosate resistance which is an excellent selection marker gene for many plants, including tomato. The gene is fused to the Arabidopsis EPSPS chloroplast transit. peptide (CTP2) and expressed from the FMV promoter as described therein.

When adequate numbers of cells (or protoplasts) containing the gene of choice driven by a promoter of the present invention are obtained, the cells (or protoplasts) are regenerated into whole plants. Choice of methodology for the regeneration step is not critical, with suitable protocols being available for many tomato varieties.

The following examples are provided to better elucidate the practice of the present invention and should not be interpreted in any way to limit the scope of the present invention. Those skilled in the art will recognize that various modifications, truncations, etc. can be made to the methods and promoters described herein while not departing from the spirit and scope of the present invention.

EXAMPLE 1

Two of these promoters have been fused to the GUS gene and transformed into tomatoes. Plasmids pMON17279 (described in Example 2), containing the potato small subunit ADPGPP promoter, and pMON17327, containing the potato patatin 1.0 (or pat1.0) promoter were used in the assay. The plant transformation vector pMON17327, containing the patatin 1.0 promoter-GUS expression cassette, was constructed as follows: the patatin 1.0 promoter (as in pMON20113, described below) was cloned as a HindIII-BglII fragment into pMON10098, disclosed in U.S. Pat. No. 5,254,801, (replacing the enhanced CAMV35S promoter) to form pMON16952. The *E. coli uidA* (GUS) gene was then cloned as BglII-EcoRI fragment downstream of the patatin 1.0 promoter in pMON16952 to form pMON17266. The CMoVb-CTP2/CP4 EPSPS-E9 3' glyphosate selection cassette as described for pMON17227 was then cloned into the NotI-XhoI sites (replacing the NptII selectable marker cassette) to form pMON17327.

Tomato plant cells were transformed utilizing Agrobacterium strains by the method as described in McCormick et al. (1986) *Plant Cell Reports* 5:80–84. In particular, cotyledons are obtained from 7–8 day old seedlings. The seeds are surface sterilized by the following procedure: 1 ) soak seeds in water for 15 min; 2) soak in 70% EtOH for 1 minute, then rinse with sterile water; 3) soak in 1N NaOH for 20 minutes; 4) rinse 2 times in sterile water; 5) soak in 25% Chlorox with Tween 20 for 25 min; 6) rinse in sterile, deionized water 3 times. The seeds are germinated in phyta trays (Sigma) on Davis germination media, as described above, with the addition of 25 mg/L ascorbic acid. The seeds are incubated for 2–3 days at 28° C. in the dark, and then grown in the growth chamber at 25° C., 40% humidity under cool white lights with an intensity of 80 einsteins m$^{-2}$s$^{-1}$. The photoperiod is 16 hrs of light and 8 hrs of dark.

Seven to eight days after initiating germination, the cotyledons are explanted as described above. The cotyledons are pre-cultured on "feeder plates" composed of Calgene media, plus acetosyringone and 1 mM galacturonic acid, containing no antibiotics, using the conditions described above.

Cotyledons are then inoculated with a log phase solution of Agrobacterium containing the plasmids described above. The concentration o the Agrobacterium is approximately 5×10$^8$ cells/ml. The cotyledons are allowed to soak in the bacterial solution for eight minutes and are then blotted to remove excess solution on sterile Whatman filter disks and are subsequently replaced to the original feeder plate where they are allowed to co-culture for 2–3 days.

Cotyledons are transferred to selection plates containing Davis regeneration media with 2 mg/l zeatin riboside, 500 µ/ml carbenicillin, and 100 µg/ml kanamycin. After 2–3 weeks, cotyledons with callus and/or shoot formation are transferred to fresh Davis regeneration plates containing carbenicillin and kanamycin at the same levels. The experiment is scored for transformants at this time. The callus tissue is subcultured at regular 3 week intervals and any abnormal structures are trimmed so that the developing shoot buds will continue to regenerate. Shoots develop within 3–4 months.

Once shoots develop, they are excised cleanly from callus tissue and are planted on rooting selection plates. These plates contain 0.5×MSO containing 50 µg/ml kanamycin and 500 µg/ml carbenicillin. These shoots form roots on the selection media within two weeks. If no shoots appear after 2 weeks, shoots are trimmed and replanted on the selection media. Shoot cultures are incubated in percivals at a temperature of 22° C. Shoots with roots are then potted when roots are about 2 cm in length. The plants are hardened off in a growth chamber at 21° C. with a photoperiod of 18 hours light and 6 hrs dark for 2–3 weeks prior to transfer to a greenhouse. In the greenhouse, the plants are grown at a temperature of 26° C. during the day and 21° C. during the night. The photoperiod is 13 hours light and 11 hours dark and allowed to mature.

When a glyphosate resistance gene is used instead of NPTII (conferring kanamycin resistance) the method differs as follows:

Cotyledons are transferred to selection plates containing Davis regeneration media with 2 mg/l zeatin riboside, 500 µg/ml carbenicillin, and 100 µg/ml cefotaxime. After 8 days, tissue is moved to fresh regeneration medium containing 0.03 mM glyphosate, 500 µg/ml carbenicillin, and 100 µg/ml cefotaxime. After 2–3 weeks, cotyledons with callus and/or shoot formation are transferred to fresh Davis regeneration plates containing glyphosate (0.05 mM), carbenicillin and cefotaxime. The experiment is scored for transformants at this time. The callus tissue is subcultured at regular 3 week intervals and any abnormal structures are trimmed so that the developing shoot buds will continue to regenerate. Shoots develop within 3–4 months.

Once shoots develop, they are excised cleanly from callus tissue and are planted on rooting selection plates containing the same level of glyphosate, carbenicillin, and cefotaxime, but with a reduced level of zeatin (1 mg/L). Benlate is also incorporated into the medium. These shoots form roots on the selection media within three weeks. Whole plants are then obtained as described above.

Regenerated tomato plants were observed for evidence of expression of GUS throughout their life cycle. The results indicated that both promoters were expressed in tomato fruit throughout development. Expression was detected from the onset of fruit development to maturity. Expression was relatively uniform throughout the fruit with strong expression detectable in all cell types including the seed. Expression appeared slightly stronger in green fruit but expression in ripe fruit may have been underestimated due to softness of the tissue that hindered the enzyme assay. Both promoters also expressed in the leaves and the stems of the transgenic tomato plants. Pat1.0 promoter expression was restricted to the cells near the vascular region of the leaf and was less intense than the expression in fruit. The small subunit ADPGPP promoter was expressed at very high levels in leaves and stems in an area surrounding the vasculature in cortical cells. Expression levels in these cells in particular were equivalent to those detected in fruit.

EXAMPLE 2

The promoters of the present invention were fused to the chimeric CTP-GlgC16 gene (and suitable 3' sequences) disclosed in WO 91/19806, and the expression cassettes were moved into a plant transformation vector, as described below.

The patatin 3.5 promoter was obtained from the plasmid pBI240.7 (Bevan et al., *Nucleic Acids Res.* 14(11):4625–4638, 1986). The majority of the 3.5 promoter was excised from pBI240.7, from the HindIII site (-3500) to the XbaI site at -337, and combined with the remainder of the promoter, from the XbaI site to a BglII site at +22 (formerly a DraI site), in a triple ligation into a vector which provided a BglII site to form pMON 17280. This latter plasmid then served as the vector for the triple ligation of the complete 3.5 promoter and the plastid target peptide-glgC16 fusion from pMON20102, described in WO 91/19806, to form the tuber expression cassette (in pMON17282). This cassette, consisting of the patatin 3.5 promoter, the plastid target peptide-GlgC16 fission, and the NOS 3' sequences, was introduced into the plant transformation vector pMON-17227, a Ti plasmid vector disclosed and described by Barry et al. in WO 92/04449, on a NotI fragment to form pMON17316.

The patatin 1.0 promoter was excised from the pBI241.3 plasmid as a HindIII-BamHI fragment (The pBI241.3 plasmid contains the patatin-1 promoter segment comprising from the AccI site at 1323 to the DraI site at 2289 [positions refer to the sequence in Bevan et al., 1986] with a HindIII linker added at the former and a BamHI linker added at the latter position; Bevan et al., 1986) and ligated together with the CTP1-glgC16 fusion (the BglII-SacI fragment from pMON20102) and a pUC-type plasmid vector cut with HindIII and SacI (these cloning sites in the vector are flanked by NotI recognition sites). The cassette was then introduced, as a NotI site in pMON886, as disclosed in U.S. Pat. No. 5,254,801, incorporated by reference herein, such that the expression of the glgC16 gene is in the same orientation as that of the NPTII (kanamycin) gene. This derivative is pMON20113.

Another vector containing the patatin 1.0 promoter was prepared from pMON10098, also disclosed in U.S. Pat. No. 5,254,801. pMON10098 was digested with HindIII and SacI. To this was added the HindIII-BamHI promoter segment described above and the CTPl-glgC16 fusion (the BglII-SacI fragment from pMON20102). This resulted in the vector pMON-16951, which contains the patatin 1.0 promoter-CTP-glgC16 cassette in a double border binary vector also containing the NPTII gene. To make this a glyphosate selection vector, the NPTII gene was removed by digesting with Not I and Xho I, and the CP4 expression cassette as described for pMON17227 above was inserted. This resulted in the vector pMON17320, which contains the FMV-CP4 cassette as a selectable marker and the patatin 1.0-CTP-glgC16 cassette, all in a binary, double border plasmid.

The promoter for the potato tuber ADPGPP small subunit gene, SEQ ID NO: 1, (Nakata et al. (1992) *J. Cell. Biochem.* Suppl. 16F, Abstract Y311, p. 266). was obtained as a XbaI-BglII fragment of the genomic clone 1–2 and inserted into the XbaI and BamHI site of Bluescript II KS-. The promoter fragment used consists of the portion from the ClaI site about 2.0 kb extending from the putative initiating methionine to the HindIII site located 12 bp before this ATG. A BglII site was placed adjacent to this HindIII site by subcloning through another pUC vector, and was linked through this latter site to the fusion of the CTP targeting and the glgC16 coding sequences. This cassette, with a NOS 3' sequence, was introduced into two vectors to provide differing transformation selection markers. pMON17279 contains both GUS and the NPTII (kanamycin) selection cassettes and pMON17354 contains the glyphosate selection cassette as in pMON17227, described above.

The promoter for the potato granule bound starch synthase (GBSS) gene (SEQ ID NO:2) was isolated from Russet Burbank DNA by PCR based on the sequence published by Rohde et al. (1990) J. Genet. & Breed. 44:311–315. PCR primers were designed to introduce a HindIII cloning site at the 5' end of the promoter, and a BglII site downstream of the transcription start site. The resultant 1.2 Kb promoter fragment was ligated into pMON10098, described in U.S. Pat. No. 5,254,801, incorporated herein by reference, in place of the E35S promoter, and fused with a BglII-SacI fragment containing the CTP1-glgC16 chimeric gene of pMON-20102, described above. The E35S-NPT II-Nos cassette was removed from this plasmid and replaced with the FMV-CP4 expression cassette, as described above, resulting in the plasmid pMON16996.

Promoters for the large subunit of potato tuber ADPGPP were isolated from two varieties of potato, Russet Burbank (SEQ ID NO:3) and Desiree (SEQ ID NO:4). The clones were identified using plaque hybridization with a probe from the 5' end of a cDNA from the large subunit of ADPglucose pyrophosphorylase. The translational start sites (ATG) of these clones were identified by plant consensus (Lutcke et al. (1987), *EMBO J.* 6(1):43–48). PCR primers were used to introduce an BamHI site at the 3' end downstream of the ATG and a HindIII site at the 5' end of both promoters. The resulting 600 bp Russet Burbank promoter and 1600 bp Desiree promoters were each ligated into pMON-10098 plasmids in place of the E35S promoter, and fused with a BglII-SacI fragment from pMON20102 containing the CTP-glgC16 chimeric gene. The E35S-NPTII-Nos cassette was removed from these plasmids and replaced with a NotI-SalI fragment of pMON17227, discussed above, resulting in pMON21522 (Russet Burbank) and pMON21523 (Desiree).

Tomato tissue was prepared and transformed with plasmids pMON-17279, pMON17320, and pMON17316, and tomato plants were regenerated as described in Example 1. One or more lines transformed with each vector were grown in plots of twenty plants under commercial conditions in a California field. Five pounds of fruit were gathered from each plot and processed. The concentrated juice was analyzed for soluble solids (Brix), paste viscosity (Bostwick), total solids, and serum viscosity. The data are reported in Table 2. The control lines (UC204C) were non-transgenic controls.

The results indicate that the small subunit ADPGPP promoter (from pMON17279) causes high expression of glgC16 in green fruit with a 2- to 10-fold decrease in red fruit. This results in significant starch in the ripe fruit (0.3–0.4% fresh weight in one line) and in viscous juice extracted from the fruit with an concomitant increase in measured solids. The patatin 1.0 promoter and the patatin 3.5 promoter are weaker, but definitely active in tomato fruit.

TABLE 2

| Line | Brix | Bostwick | % Tot. solids | Ser. visc. |
|---|---|---|---|---|
| 17320-8674 | 4.0 | 14.55 | 4.78 | 6.421 |
| 17316-9302 | 4.3 | 16.85 | 4.98 | 5.893 |
| 17279-10120 | 4.6 | 15.40 | 5.36 | 7.951 |
| 17279-10245 | 4.5 | 14.00 | 5.30 | 6.455 |
| 17279-10246 | 4.7 | 13.00 | 5.53 | 6.796 |
| 17279-10272 | 4.6 | 15.15 | 5.32 | 7.998 |
| 17279-10309 | 4.3 | 14.70 | 5.14 | 6.079 |
| 17279-9858 | 4.3 | 10.90 | 5.33 | 6.521 |
| 17279-10076 | 4.6 | 12.40 | 5.49 | 6.435 |
| 17279-10205 | 4.2 | 13.05 | 5.04 | 4.558 |
| 17279-10279 | 4.2 | 13.55 | 4.98 | 4.096 |
| 17279-10307 | 4.0 | 11.30 | 4.98 | 4.061 |
| 17279-10356 | 4.4 | 12.75 | 5.22 | 4.848 |
| UC204C control | 4.1 | 15.80 | 4.85 | 6.518 |
| UC204C control | 4.1 | 15.80 | 4.67 | 5.561 |
| UC204C control | 4.0 | 14.65 | 4.76 | 5.967 |
| UC204C control | 4.0 | 14.65 | 4.78 | 5.652 |
| UC204C control | 4.1 | 14.60 | 4.78 | 5.564 |
| UC204C control | 4.2 | 14.45 | 4.87 | 5.463 |

All publications and patents mentioned in this specification are herein incorporated by reference as if each individual publication or patent was specifically and individually stated to be :incorporated by reference.

From the foregoing, it will be seen that; this invention is one well adapted to attain all the ends and objects hereinabove set forth together with advantages which are obvious and which are inherent to the invention.

It will be understood that certain features and subcombinations are of utility and may be employed without reference to other features and sub-combinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

We claim:

1. A method of causing expression of a protein or an antisense mRNA in the fruit of tomato plants comprising: (1) transforming tomato plant cells with a DNA construct comprising in operative order: (a) a promoter selected from the group consisting of patatin promoters and potato ADPGPP promoters; (b) a structural DNA sequence that causes the production of an RNA sequence; and (c) a 3' non-translated region which functions in plant cells to cause transcriptional termination and the addition of polyadenylated nucleotides to the 3' end of the RNA sequence; (2) regenerating tomato plants containing said DNA construct; and (3) obtaining fruit in which the structural DNA sequence is expressed.

2. The method of claim 1 wherein said structural DNA sequence is in antisense orientation.

3. The method of claim 1 wherein said structural DNA encodes ADPglucose pyrophosphorylase.

4. The method of claim 3 wherein said ADPglucose pyrophosphorylase is glgC16.

5. The method of claim 1 wherein said promoter is the small subunit ADPGPP promoter.

6. The method of claim 4 wherein said promoter is the small subunit ADPGPP promoter.

7. A tomato plant cell comprising a recombinant, double-stranded DNA molecule comprising in sequence:

(a) a promoter selected from the group consisting of patatin promoters and potato ADPGPP promoters;

(b) a structural DNA sequence that causes the production of an RNA sequence; and (c) a 3' non-translated region which functions in plant cells to cause transcriptional termination and the addition of polyadenylated nucleotides to the 3' end of the RNA sequence, wherein said promoter causes expression of said structural DNA sequence in the fruit sequence is in antisense orientation.

8. The tomato plant cell of claim 7 wherein said structural DNA sequence is in antisense orientation.

9. The tomato plant cell of claim 7 wherein said structural DNA sequence encodes ADPglucose pyrophosphorylase.

10. The tomato plant cell of claim 9 wherein said ADPglucose pyrophosphorylase is glgC16.

11. The tomato plant cell of claim 7 wherein said promoter is the small subunit ADPGPP promoter.

12. The tomato plant cell of claim 10 wherein said promoter is the small subunit ADPGPP promoter.

13. A tomato plant consisting of cells of claim 7.

14. A tomato plant consisting of cells of claim 12.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2196 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
ATCGATTATT  GGTTTATCGG  GTTTTGATCG  TTATCGGTTC  GGTTTAACCG  TTAAAATTTG     60
ACACAAAAAT  AAAAATTGAA  AAGCACTTAG  AAACAAGGTG  ACAAACCTAA  TAAACCATGC    120
ACATGAGTTC  ACAAGTTACA  TCTTGCTAAA  AAACAAACAC  TTTTACATTG  TAGAATAACC    180
AAGTGTCTGG  GACAACCAAA  AATGAAAGTA  GGAAACCAAA  CTCTAAGTCA  AGGACTTTAT    240
ATACAAAATG  GTATAACTAT  AATTATTTAA  TTTACTATTG  GGTTATCGGT  TAACCCGTTA    300
AGAACCGATA  ACCCGATAAC  AAAACAATC   AAAATCGTTA  TCAAAACCGC  TAAACTAATA    360
ACCCAATACT  GATAAACCAA  TAACTTTTTT  TTTATTCGGG  TTATCGGTTT  CAGTTCGGTT    420
TTGAACAATC  CTAGTGTCCT  AATTATTGTT  TTGAGAACCA  AGAAAACAAA  AACTGACGTC    480
GCAAATATTT  CAGTAAATAC  TTGTATATCT  CAGTGATAAT  TGATTTCCAA  GATGTATAAT    540
TATCATTTAC  GTAATAATAG  ATGGTTTCCG  AAACTTACGC  TTCCCTTTTT  TCTTTTGCAG    600
TCGTATGGAA  TAAAGTTGGA  TATGGAGGCA  TTCCCGGGCC  TTCAGGTGGA  AGAGACGGAG    660
CTGCTTCACA  AGGAGGGGGT  TGTTGTACTT  GAAAATAGGC  ATTTATTCCG  TTCGCAAACC    720
TATCATGTTC  CTATGGTTGT  TTATTTGTAG  TTTGGTGTTC  TTAATATCGA  GTGTTCTTTA    780
GTTTGTTCCT  TTTAATGAAA  GGATAATATC  TCGTGCCAAA  AATAAGCAAA  TTCGGTACAT    840
AAAGACATTT  TTTTTCTTTC  GTGGATTTTC  TGTTTATGGA  GTTGTCAAAT  GTGGAATTTA    900
TTTCATAGCA  TGTGGAGTTT  CCTCCTCTCC  TTTTTCATGT  GCCCTTGGGC  CTTGCCTGTT    960
TCTTGCACCG  CAGTGTGCCA  GGGCAGTCGG  CAGATGGACA  TAAATGGCAC  ACCGCTCGGC   1020
TCGTGGAAAG  AGTATGGTCA  GTTTCATTGA  TAAGTATTTA  CTCGTATTCG  GCGTATACAT   1080
CAAGTTAATA  GAAAGTAAAC  ACATATGATA  TCATACATCC  ATTAGTTAAG  TATAAATGCC   1140
AACTTTTTAC  TTGAATCGCT  GAATAAATTT  ACTTACGATT  AATATTTAGT  TGTGTGTTCA   1200
AACATATCAT  GCATTATTTG  ATTAAGAATA  AATAAACGAT  GTGTAATTTG  AAAACCAATT   1260
AGAAAAGAAG  TATGACGGGA  TTGATGTTCT  GTGAAATCAC  TGGCAAATTG  AACGGACGAT   1320
GAAATTTGAT  CGTCATTTAA  ACATATCAAC  ATGGCTTTAG  TCATCATCAT  TATGTTATAA   1380
TTATTTTCTT  GAAACTTGAT  ACACCAACTC  TCATTGGGAA  AGTGACAGCA  TAATATAAAC   1440
TATAATATCA  ATCTGGCAAT  TTCGAATTAT  TCCAAATCTC  TTTTGTCATT  TCATTTCATC   1500
CCCTATGTCT  GCCTGCAAGT  ACCAATTATT  TAAATACAAA  AATCTTGATT  AAACAATTCA   1560
TTTTCTCACT  AATAATCACA  TTTAATAATA  AACGGTTCAT  ACACGTGCGT  CACCTTTTTT   1620
TCGATTTTCT  CTCAAGCGCA  TGTGATCATA  TCTAACTCTT  GTGCAAACAA  GTGAAATGAC   1680
GTCCATTAAT  AAATAATCTT  TTGAATACCT  GTTCATTTTA  ATTTATTGG   ATTTGCTAAG   1740
GATTTTTTT   AGTTTTGAG   ATTTTTATA   ATTTAAATT   AAAAAAAATA  AGTTAAATAT   1800
ATCGAAAATG  TCTTTTAATC  TTATTTTTGA  AAAAGATAAT  TAGCTCAAAC  AAATTAAAAT   1860
TGGTAACTAT  TTTTCGGAAA  AATAATGATT  CTTATTGTAC  ATTCTTTTTC  ATCGATTAGA   1920
TATTTTTTTT  AAGCTCAAGT  ACAAAAGTCA  TATTTCAATC  CCCAAAATAG  CCTCAATCAC   1980
```

| | | | | | |
|---|---|---|---|---|---|
| AAGAAATGCT | TAAATCCCCA | AAATACCCTC | AATCACAAAA | AGTGTACCAA | TCATAACTAT | 2040
| GGTCCTCTGT | AAATTCCAAC | AAAATCAAGT | CTATAAAGTT | ACCCTTGATA | TCAGTACTAT | 2100
| AAAACCAAAA | ATCTCAGCTG | TAATTCAAGT | GCAATCACAC | TCTACCACAC | ACTCTCTAGT | 2160
| AGAGAAATCA | GTTGATAACA | AGCTTTGTTA | ACAATG | | | 2196

( 2 ) INFORMATION FOR SEQ ID NO:2:

( i ) SEQUENCE CHARACTERISTICS:
        ( A ) LENGTH: 1226 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

| | | | | | |
|---|---|---|---|---|---|
| AAGCTTAAGC | GGTAACGAGA | TAGAAAATTA | TATTACTCCG | TTTTGTTCAT | TACTTAACAA | 60
| ATGCAACAGT | ATCTTGTACC | AAATCCTTTC | TCTCTTTTCA | AACTTTTCTA | TTTGGCTGTT | 120
| GACAGAGTAA | TCAGGATACA | AACCACAAGT | ATTTAATTGA | CTCCTCCGCC | AGATATTATG | 180
| ATTTATGAAT | CCTCGAAAAG | CCTATCCATT | AAGTCCTCAT | CTATGGATAT | ACTTGACAGT | 240
| TTCTTCCTAT | TTGGGTGTTT | TTTTCCTGTT | AAGTGGAACG | GAGACATGTT | ATGATGTATA | 300
| CGGGAAGCTC | GTTAAAAAAA | AAAAAACAAT | AGGAAGAAAT | GTAACAAACA | TTGAATGTTG | 360
| TTTTTAACCA | TCCTTCCTTT | TAGCAGTGTA | TCAATTTTGT | AATAGAACCA | TGCATCTCAA | 420
| TCTTAATACT | AAAAAATGCA | ACTTAAGATA | GGCTAAACCA | AGTAAAGTAA | TGTATTCAAC | 480
| CTTTAGAATT | GTGCATTCAT | AATTTGATCT | TGTTTGTCGT | AAAACATTAG | AAAATATATT | 540
| TACAGTAATT | TGGAATACAA | AGCTAAGGGG | GAAGTAACTA | CTAATATTCT | AGTGGAGGGA | 600
| GGGACCAGTA | CCAGTACCTA | GATATTATTT | TTAATTACTA | TAATAATAAT | TTAATTAACA | 660
| CGAGACATAG | GAACGTCAAG | TGGTAGCGGT | AGGAGGGAGT | TGGTTTAGTT | TTTTAGATAC | 720
| TAGGAGACAG | AACCGGACGG | GCCCATTGCA | AGGCCCAAGT | TGAAGTCCAG | CCGTGAATCA | 780
| ACAAAGAGAG | GGCCCATAAT | ACTGTCGATG | AGCATTTCCC | TATAATACAG | TTGCCTTCCA | 840
| CTAAGGGATA | GTTACCCGCA | ATTCTCTTGA | CACGTGTCAC | TGAAACCTGC | TACAAATAAG | 900
| GCAGGCACCT | CCTCATTGAC | ACTCACTCAC | TCACTCACTC | ACACAGCTCA | ACAAGTGGTA | 960
| ACTTTTACTC | ATCTCCTCCA | ATTATTTATG | ATTTCATGCA | TGTTTCCCTA | CATTCTATTA | 1020
| TGAATCGTGT | TATGGTGTAT | AAACGTTGTT | TCATATCTCA | TCTCATCTAT | TCTGATTTTG | 1080
| ATTCTCTTGC | CTACTGTAAT | CGGTAATAAA | TGTGAATGCT | TCCTCTTCTT | CTTCTTCTCA | 1140
| GAAATCAATT | TCTGTTTTGT | TTTTGTTCAT | CTGTAGCTTA | TTCTCTGGTA | GATTCCCCTT | 1200
| TTTGTAGACC | ACACATCACA | AGATCT | | | | 1226

( 2 ) INFORMATION FOR SEQ ID NO:3:

( i ) SEQUENCE CHARACTERISTICS:
        ( A ) LENGTH: 591 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

| | | | | | |
|---|---|---|---|---|---|
| AAGCTTGATA | TCGAATTCCT | GCAGCCCGGG | GGATCTCCTT | AAAACTTTTT | CTGAATTACT | 60
| TTTCAAGATT | CTTGATTCTG | CACCACTAGC | AATTTCCATT | TTCTTTCAG | TGATTTTGGT | 120

-continued

| | | | | | |
|---|---|---|---|---|---|
| TACTTATTTG | ACATTCTTGT | TTTCAAGATC | CAACATCATC | ACTTTCCAGG | TTCAAAATCT | 180 |
| TGTTTTTTTT | CTTTTTTCTT | TTAATGCTCT | ATATTGTGGA | AGTCCACAGG | TGAATTTTTA | 240 |
| CGATATGGGT | TTACCACTTA | GCTTCTTGT | AATATTTTAT | CAATTTTAGA | AAATATATGT | 300 |
| GTGAAATACC | TAATTTTACG | TAGAGATCAT | GGGTTCATAT | GCGTAAAGAT | TCATGTTTTT | 360 |
| GTGGTAATGC | TATGAGGTAT | TAGTACTGAG | CATATAGCTA | GCTTGGGTTT | TGGGTTTACC | 420 |
| GACCAAAAAA | AAAAATTAGT | GATATTTCT | TTATGTAAAT | TATACTTTTC | TTGGTTGCTA | 480 |
| AAAGATAACA | TATACTTTAT | TGAGATTTGA | ATAAATCTAT | TTGATTTAGA | TCCATTGATA | 540 |
| AATCTTAATC | TTATGGGATT | ACTGATTTGT | TGATTGGCTG | CAGAAGGATC | C | 591 |

( 2 ) INFORMATION FOR SEQ ID NO:4:

( i ) SEQUENCE CHARACTERISTICS:
( A ) LENGTH: 1705 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:4:

| | | | | | |
|---|---|---|---|---|---|
| AAGCTTGGGT | ACCGGGCCCC | CCCTGGAGGT | CGAGTGCCAT | CACATCCAGG | GTGTAGGCTC | 60 |
| GGGGCGTGAC | AAACTTGGTA | TCTGAGCTCA | GAGTTCAAGA | GTCTAAGGTG | TCTATAAAGT | 120 |
| CTGTGCCTTT | AGAGTCCTAG | TTATCGGTGT | GAAGCGCGCC | ACATCTATAA | CCAGGAGGCT | 180 |
| GCGACATTTA | AGAATTATCA | TACTTCTTTC | ATACTCTTTT | CGTGCAATAG | AGTTCAACTC | 240 |
| CATAAAGTCT | CTTTATAATT | CATGTTTACG | CATATCTTTG | AGATCATGCC | TCCATGTAGA | 300 |
| GTTGTCTGAG | GTCGTCCTGC | TAGAAGAAAT | ATTGATCCTC | AGGATCAAGG | GGTACCCAAT | 360 |
| GCACCAGAAG | TGCGACCCCA | AGGAAAGGTC | ACTAATGTTG | AGTTCCAGGA | TGTTATACGG | 420 |
| ATATTGAGTG | AAGTTGTGAC | CAACCAAGCT | GGACAACAAA | GAGGGAATCA | ACAAGATGTG | 480 |
| GTTGATACAT | CCAGAATCCG | TGAGTTCTTA | AGGATGAATC | CTTCAGACTT | CACCAATTCA | 540 |
| AGAGTCACTG | AGGATCTGGA | AAACTTTGTG | GAAGAGTTGT | AGAAGGTTTT | TGAGGTTATG | 600 |
| CATGTTGTTG | ATGCTGAGCG | AGTGGAACTA | ACTGCATACC | AACTGAATGG | TGTTGCTAGA | 660 |
| GTATGGTACG | ACCAATAGAA | AAAGAGTAGA | GTTGAGGGTG | CACAAATTGT | GAGTTGGGCA | 720 |
| GTGTTTGAAG | AGGCCTTCAT | GGGGCATTTC | TTTTCCCATG | AACTATATGG | CAAAGGTAAG | 780 |
| AGAATTTCCT | CACTCTTAAG | CAGGAATCCA | TGAGTGTGCA | TAAGTATAGC | CTCAAGTTCA | 840 |
| CTCAACTGTC | GCCTATGCTC | CAGAGATGGC | TGTTGATATG | AGGAGCAGGA | TGGGCTTGTT | 900 |
| TGTGTTTGGG | TTGTCTCATC | TGTCAATCAA | AGAAGGTAAG | GTTGTGATGT | GGATAAAGGA | 960 |
| CATGGACATC | GAAAGGGTAA | TGATCCTTGT | GCAACAGGTT | GAGGAAGATA | AGTTGAGGGA | 1020 |
| TAGAGAAGAG | TTCTGAAACA | AGAGGGCTAA | GAACACATGA | AATGAGTACG | TAAGCAGAAG | 1080 |
| AGTAATGCAA | ATCGGTTATC | TTTTCAATGA | AAGCCAAATA | AACCTGCTTG | ATTGTTTGCA | 1140 |
| AGTGCAACCT | GTACCAACGA | ACAAGGTGA | GTTCAAGAAT | CAGAATTCTT | AGAAATTCAG | 1200 |
| AGCTAGACCT | GCACAATCTC | AAGGTAGTGT | GGCACAAGGA | TGTAATGGGA | CTCCTGCATG | 1260 |
| TGTTAAGTAC | GGTAGGAACC | ACCCAGGAGC | GTGTCATGAT | GGCTCTGCTG | GTTGCTTCAA | 1320 |
| GTGTGGTCAG | AATGGTCACT | TCATGAGAGA | GTGCCTAAAG | AANAGGCAAG | GTAATAGCAA | 1380 |
| TGGGGGCAAT | ATATCACAAT | CTTCTTCAGT | GGCTCCACNA | GATAGAGCTG | CACCTTGAGG | 1440 |
| ATCATGGGTT | CATATGCGTA | AAGATTCATG | TTTTGTGGTA | ATGCTATGAG | GTATTAGTAC | 1500 |
| TGAGCATATA | GCTAGCTTGG | GTTTTGGGTT | TACCGACCAT | TTTTTTTAAT | TAGTGATATT | 1560 |

```
TTCTTTATGT  ATTTTATACT  TTTCTTGGTT  GCTTAAAGAT  TACATATACT  TTATTGAGAT   1620

TTGAATAAAT  CTATTTGATT  TAGATCCATT  GATAAATCTT  AATCTTATGG  GATTACTGAT   1680

TTGTTGATTG  GCTGCAGAAG  GATCC                                            1705
```